(12) United States Patent
Roper

(10) Patent No.: US 10,753,837 B2
(45) Date of Patent: Aug. 25, 2020

(54) DEVICE FOR COLLECTING AND ENRICHING MICROBES

(71) Applicant: The Board of Trustees of the University of Arkansas, Little Rock, AR (US)

(72) Inventor: Donald Keith Roper, Fayetteville, AR (US)

(73) Assignee: The Board of Trustees of the University of Arkansas, Little Rock, AR (US)

(*) Notice: Subject to any disclaimer, the term of this patent is extended or adjusted under 35 U.S.C. 154(b) by 90 days.

(21) Appl. No.: 15/988,833

(22) Filed: May 24, 2018

(65) Prior Publication Data

US 2018/0340871 A1 Nov. 29, 2018

Related U.S. Application Data

(60) Provisional application No. 62/511,097, filed on May 25, 2017.

(51) Int. Cl.
*G01N 1/40* (2006.01)
*C08J 3/075* (2006.01)
*C12Q 1/24* (2006.01)

(52) U.S. Cl.
CPC .............. *G01N 1/405* (2013.01); *C08J 3/075* (2013.01); *C12Q 1/24* (2013.01); *C08J 2333/24* (2013.01)

(58) Field of Classification Search
CPC ........ A61B 18/203; A61B 2018/00047; A61B 2018/00476; A61B 2018/00577; A61B 17/50; A61B 18/06; A61B 18/18; A61B 2018/00452; A61B 2018/00458; A61B 2018/00791; A61B 2018/00809; A61B 2018/068; A61B 17/54; A61B 2017/00747; A61B 2017/00752; A61B 5/065; A61B 1/00; A61B 1/00009; A61B 1/041; A61B 2034/2051; A61B 2034/2063; A61B 2034/2072; A61B 2090/3929; A61B 2090/3966; A61B 2562/162; A61B 2562/168; A61B 50/13; A61B 5/0024; A61B 5/0028; A61B 5/062; A61B 5/073; A61B 5/14507; A61B 5/14539; A61B 5/4238; A61B 5/6852; A61B 5/6853; A61B 5/6861; A61B 5/742; A61B 8/0833; A61B 8/461; A61B 8/56; A61B 2034/2055; A61B 2090/3945; A61B 34/20; A61B 5/4887; A61B 90/39; A61K 2800/413; A61K 2800/621; A61K 2800/624; A61K 2800/81; A61K 8/0245; A61K 8/0283; A61K 8/29; A61K 9/0009; A61K 9/0014; A61K 9/009; A61K 9/5115; A61K 2800/622; A61K 41/0052; A61K 41/0057; A61K 8/0241; A61K 8/11; A61K 8/19; A61K 9/5123; A61K 9/5146; A61K 9/5153; A61K 41/0047; A61K 9/0019; A61K 9/0024; A61K 9/146; A61K 47/26; A61K 47/42; A61N 2005/0659; A61N 2005/067; A61N 5/0616; A61N 5/062; A61N 2007/0034; A61N 5/0617; A61N 5/0624; A61N 5/0625; A61N 7/00; A61Q 19/06; A61Q 19/08; A61Q 9/04; A61Q 19/00; A61Q 9/00; B82Y 5/00; B82Y 15/00; B82Y 30/00; B22F 1/004; B22F 2999/00; B22F 2998/00; B22F 7/06; B22F 9/16; B22F 2998/10; B22F 1/0018; B22F 2207/01; B22F 3/002; B22F 3/20; B22F 5/12; B22F 1/0025; B22F 1/02; B22F 1/025; C07D 501/04; C07D 501/16; C07D 501/18; C07D 519/06; C12Q 1/34; C12Q 1/6818; C12Q 1/24; G01N 2021/6439; G01N 21/6428; G01N 21/648; G01N 21/6486; G01N 21/658; G01N 2201/06113; G01N 2333/986; G01N 33/54353; G01N 33/56911; G01N 33/56916; G01N 33/56938; G01N 33/56983; G01N 2610/00; G01N 33/54346; G01N 33/54366; G01N 33/54386; G01N 33/553; G01N 1/405; B01L 3/502753; B01L 2200/10; B01L 2400/0454; B01L 3/502707; B01L 7/52; B29C 2059/028; B29C 2071/0018; B29C 2071/0054; B29C 37/0032; B29C 59/022; B29C 70/64; B29C 71/0009; B29K 2105/0023; B29K 2995/0005; C25D 7/00; Y10T 428/25; Y10T 428/254; Y10T 29/49801; A61M 37/0092; A61M 2025/1054; B01D 2325/26; B01D 67/0041; B01D 67/0058; B01D 69/145; B01D 71/022; B01J 35/06; B21C 1/003; B21C 37/047; C12M 23/16;
(Continued)

(56) References Cited

U.S. PATENT DOCUMENTS 9,433,677 B2* 9/2016 Harris .................... A61Q 19/00
2016/0296933 A1* 10/2016 Chiou ............... B01L 3/502738
(Continued)

*Primary Examiner* — Deborah K Ware
(74) *Attorney, Agent, or Firm* — J. Clinton Wimbish; Nexsen Pruet, PLLC

(57) ABSTRACT

In one aspect, devices for collecting and enriching microbes are described herein. In some embodiments, such a device comprises a shape memory gel and a plurality of nanoantennas dispersed in the gel. The nanoantennas can be non-uniformly dispersed in the gel. Additionally, the nanoantennas are operable to receive an external signal and thereby induce a local change in state of the gel, such as a local change in thermodynamic state of the gel.

14 Claims, 1 Drawing Sheet

(58) Field of Classification Search
CPC ....... C12M 45/07; C12M 47/06; C12N 13/00;
C12N 1/066; H01C 3/00; H01G 4/28;
A61F 5/003; A61F 5/0036; A61F 5/0003;
A61F 5/0013; A61F 5/004; A61F 5/0043;
A61F 5/0046; A61F 5/0076; A61F
5/0089; C08J 2333/24; C08J 3/075; C07K
14/43518; C07K 14/43586; D01F 4/02;
C09K 8/5045; C09K 8/5083; C09K
8/516; C09K 8/805; C09K 8/845; C09K
8/882; C09K 8/92; E21B 43/267
See application file for complete search history.

(56) References Cited

U.S. PATENT DOCUMENTS

2018/0050109 A1* 2/2018 Kaplan ............ C07K 14/43518
2018/0340871 A1* 11/2018 Roper .................... G01N 1/405

* cited by examiner

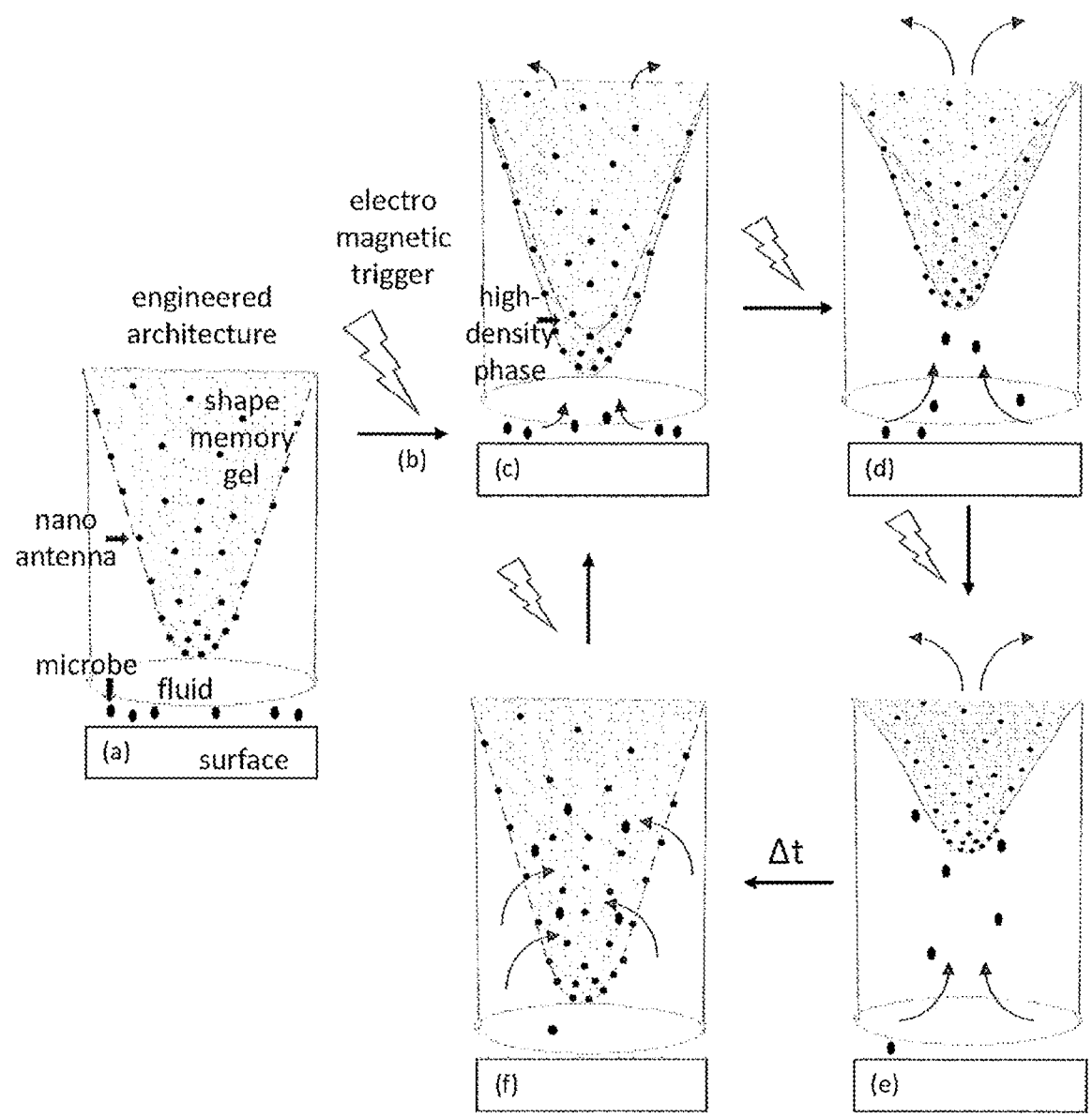

DEVICE FOR COLLECTING AND ENRICHING MICROBES

RELATED APPLICATION DATA

The present application claims priority to U.S. Provisional Patent Application Ser. No. 62/511,097 filed May 25, 2017 which is incorporated herein by reference in its entirety.

FIELD

This invention relates to the collection, enrichment, and/or analysis of microbes and, in particular, to devices and methods for collecting, enriching, and/or analyzing microbes.

BACKGROUND

Robust collection of a microbe from a native environment and its subsequent enrichment to support definitive identification is prerequisite to detection of pathogens in order to diagnose and treat disease, avoid contamination of products produced for human consumption or use, and characterize natural systems. Microbe detection has been limited by low collection efficiencies as well as by energy—and time-intensive enrichment processes. These barriers diminish the ease and reproducibility of microbial sampling, contributing to the cost and complexity of devices and procedures required.

Therefore, there exists a need for improved devices and methods for the collection, enrichment, and/or analysis of microbes.

SUMMARY

This disclosure describes robust collection and enrichment in a single engineered smart material system. In some cases, the material system includes a shape memory gel with an externally tunable capacity to absorb fluid, retain fluid-borne microbes, and subsequently expel fluid across multiple cycles to enrich microbes to a concentration sufficient for immediate, robust analysis. Analysis may be performed in situ or subsequent to discharge of retained microbes into a carrier fluid. The system includes the architecture or container designed to support the gel and its tunable functionality. Thus, a novel, smart system or device is described herein that can collect and enrich microbes to detectable levels in a single operation for rapid analysis. The device's compact size and streamlined operation reduce cost and complexity of microbe sampling, minimize sample damage, and provide flexibility for incorporation into a variety of systems. For instance, devices described herein can be used to diagnose disease, treat disease, avoid contamination of products produced for human consumption or use, and/or characterize microbes in natural systems. Additionally, in some cases, devices described herein can be used to engineer nanoinduceble tissues, tissue scaffolds, diagnostics or drug delivery vehicles.

In one aspect, devices for collecting and/or enriching microbes are described herein. In some embodiments, such a device comprises a shape memory gel and a plurality of nanoantennas dispersed in the gel. In some instances, the nanoantennas are non-uniformly dispersed in the gel, where the "non-uniform" dispersion refers to the spatial distribution of the nanoantennas within the gel. In other embodiments, the nanoantennas are uniformly dispersed in the gel. Additionally, the nanoantennas are operable to receive an external signal and thereby induce a local change in state of the gel. It is further to be understood that the local change in state can be a local change in a thermodynamic state of the gel. For example, in some cases, the local change in state induced by the nanoantennas is a local change in the internal energy, entropy, mass, chemical composition, fugacity, temperature, pH, pressure, and/or specific volume of the gel.

Moreover, in some embodiments, the gel is a pH-responsive shape memory gel, a temperature-responsive shape memory gel, a pressure-responsive shape memory gel, a light-responsive shape memory gel, or an electrochemical-responsive shape memory gel. In some instances, the gel is a crosslinked hydrogel. One non-limiting example of a shape memory gel suitable for use in some embodiments described herein is poly(N-isopropylacrylamide). Other shape memory gels may also be used.

The nanoantennas of a device described herein, as illustrated further below, can have any structure and be formed from any material suitable to selectively receive an external signal or input (such as may be provided by electromagnetic radiation or an alternating magnetic field, for example), and to translate or transform the signal into a change in state of the gel in the immediate environment of the nanoantenna. For instance, in some cases, the nanoantennas are formed from metal nanoparticles such as gold (Au) or silver (Ag) nanoparticles. As described further hereinbelow, such nanoparticles can absorb electromagnetic radiation of a certain wavelength to a greater degree or at a faster rate than the shape memory gel itself or other surrounding materials. Moreover, in such instances, the metal nanoparticles can be selectively heated by application of or exposure to the electromagnetic radiation. The incident electromagnetic radiation may thus serve as an external signal described herein. Such selective heating of the metal nanoparticles can in turn provide localized heating of the gel through heat transfer from the heated metal nanoparticle to the gel. Other methods of providing an antenna effect may also be used.

Additionally, in some cases, nanoantennas described herein can have a size or average size in one, two, or three dimensions of less than 1000 nm, less than 500 nm, less than 300 nm, less than 200 nm, less than 100 nm, less than 50 nm, or less than 10 nm. Moreover, the nanoantennas can be individual nanoparticles or arrays or secondary structures formed from a combination or agglomeration of a plurality of individual nanoparticles. Not intending to be bound by theory, it is believed that nanoantennas having a size described herein, in some instances, can provide localized heating of the gel with nanoscale resolution. In this manner, nanotunable shape memory gel materials (such as electromagnetically nanotunable materials) can be obtained.

Some non-limiting examples of materials suitable for use as nanoantennas in a shape memory gel described herein are described in Dunklin, J. R. and Roper, D. K., "Heat Dissipation of Resonant Absorption in Metal Nanoparticle-Polymer Films Described at Particle Separation Near Resonant Wavelength," *Journal of Nanomaterials* (2017), 2017, 2753934; and Roper, D. K., Ahn, W., Taylor, B., D'Asen, Y. "Enhanced spectral sensing by electromagnetic coupling with localized surface plasmons on subwavelength structures," *IEEE Sensors Journal* (2010) 10(3) 531-540, which are hereby incorporated by reference in their entireties. Other materials may also be used.

Moreover, in some cases, the nanoantennas of a device described herein are present in a shape memory gel in a higher density in a peripheral region of the gel and in a lower density in an interior region of the gel. Further, in some such instances, the peripheral region of the gel is adjacent to an intake side or region of the gel. Such an "intake" side or region of the gel can be placed in fluid communication with a liquid analyte, such as a liquid that may contain or does contain microbes, including microbes that are desired to be collected and/or concentrated, as described further hereinbelow.

Additionally, in some embodiments, a device described herein further comprises a container or architecture. More particularly, in some cases, the gel is disposed in the container. The use of such a container, in some instances, can facilitate placement of the intake side of the gel in fluid communication with a liquid or fluid sample or analyte. The use of a shaped container or architecture can also maintain a desired shape or configuration of a gel described herein, which may be desirable for peristaltic pump or other applications relying on directional movement of materials into or out of a gel described herein.

In another aspect, methods of collecting microbes from an environment, and optionally enriching and/or analyzing the microbes, are described herein. In some embodiments, such a method comprises contacting a device with a test fluid, wherein the test fluid contains or may contain microbes, and wherein the device comprises a shape memory gel device described herein. For example, in some cases, the device comprises a shape memory gel and a plurality of nanoantennas non-uniformly dispersed in the gel, the nanoantennas being operable to receive an external signal and thereby induce a local change in state of the gel. More generally, any device described hereinabove may be used.

Additionally, a method described herein, in some instances, further comprises providing an external signal to the nanoantennas to induce a local change in state of the gel. Moreover, in some embodiments, inducing the local change in state of the gel causes microbes from the test fluid to enter the gel at an intake side of the gel. Further, in some cases, a method described herein also comprises providing one or more additional signals to the nanoantennas to induce one or more additional local changes in state of the gel. Inducing the one or more additional local changes in state of the gel can cause additional microbes from the test fluid to enter the gel at the intake side of the gel. Moreover, in some instances, inducing the one or more additional local changes in state of the gel causes an analyte fluid to be expelled from the gel at an output side or region of the gel. It is to be understood that the output side or region of the gel is opposite the intake side or region of the gel. Thus, in some cases, a method described herein includes using the shape memory gel as a peristaltic pump for the collection and/or enrichment or concentration and/or analysis of microbes.

Further, in some embodiments, a method described herein also comprises measuring the amount or concentration of microbes present in a fluid expelled from the gel. A method described herein may also include determining the identity of one or more microbes disposed in the fluid.

These and other embodiments are described in greater detail in the detailed description which follows.

BRIEF DESCRIPTION OF THE DRAWINGS

FIGS. 1(a)-(f) illustrate steps of a method of collecting and enriching microbes according to one embodiment described herein.

DETAILED DESCRIPTION

Embodiments described herein can be understood more readily by reference to the following detailed description, examples and drawings and their previous and following descriptions. Elements, apparatus and methods described herein, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

Some exemplary embodiments will now be further described, including with reference to the figures.

Shape memory gels are among an emerging family of smart materials whose functionality is inducible by a change in thermodynamic state that results in altered physicochemical properties such as appearance, size, shape, flexibility, phase, chemistry, optoelectronic activity or other measurable attribute. The change in thermodynamic state (e.g., energy, entropy, mass, chemical composition, fugacity, specific volume, pressure, temperature) may be induced by one or more of a variety of means (e.g., mechanical, thermal, physicochemical, electromagnetic). Commonly used triggers are temperature, pH, pressure, light, or electrochemical stimuli. Poly(N-isopropylacrylamide), or PNIPAm, a cross-linked polymer hydrogel that changes phase when heated above thirty-two degrees Celsius, transitioning from a swollen hydrated state to a shrunken (up to ninety percent) dehydrated state, is an illustrative example. Applications considered for shape memory gels include switching, actuation, logic-gate operations, functional surfaces, sensing, microfluidic circuits, separations, and biomedical uses such as controlled drug release, engineered tissues or scaffolds, and imaging. However, utility of shape memory gel systems considered to date has been limited by the functionality, scale and interactivity of the gel, its supporting architecture, and corresponding trigger.

This disclosure describes integrating nanoantenna with tunable electromagnetic activity at subwavelength scales into gels in an architecture that supports collection and concentration of targeted microbe(s) via smart cycling of fluid intake, microbe retention, and fluid output. Retained microbe(s) may be analyzed in situ or upon discharge into a carrier fluid.

Nanoantennas are designed to have tunable electromagnetic activity at subwavelength scales in the gel, its constituent fluid and analyte(s). In some cases, computer simulation of the nanoantenna-gel-fluid composite in an externally applied electromagnetic field may be used to select a specific nanoantenna structure. Such simulation tools are described, for example, in G. T. Forcherio, P. Blake, M. Seeram, D. DeJarnette, D. K. Roper, Coupled dipole plasmonics of nanoantennas in discontinuous, complex dielectric environments, *Journal of Quantitative Spectroscopy & Radiative Transfer* (2015), 166, 93-101; D. DeJarnette, P. Blake, G. T. Forcherio, D. K. Roper, Far-field Fano resonance in nanoring lattices modeled from extracted, point dipole polarizability, *Journal of Applied Physics* (2014), 115, 024306. The suite of simulation tools, candidate architectures, and nanoantenna-polymer composites developed by the inventor has demonstrated the ability to trigger a measurable change in thermodynamic state by an external field that results in tunable polymer expansion, fluid intake, fluid output and pathogen retention across multiple cycles.

Devices and methods described herein provide measurable enhancements in electromagnetic activity, fluid dynamics, and microbe accumulation relative to alternative approaches. Again not intending to be bound by theory, it is believed that enhancements accrue from one or more of the subwavelength scale of tunable electromagnetic activity, the composition and geometry of the nanoantenna, polymer and composite, and novel transport modes and sorption chemistries.

Nanoantennas described herein enable local tunability of shape memory gel at nanometer scales. This supports precise spatiotemporal control of local state (e.g., density) to achieve dynamics that are not possible with current triggers which effect state changes at microscales or greater. A novel spatiotemporal dynamic to support microbe collection and enrichment identified in this disclosure is nanoantenna-enabled peristalsis. Peristalsis is a biological dynamic in which soft material is alternately constricted and relaxed to squeeze fluid through a channel. The peristaltic wavelike pulse provides smooth, localized, energy-efficient nearly unidirectional flow that can accommodate a high percentage of solids. It obviates the need for electrical contacts or mechanical parts that form a basis for conventional pump mechanisms. It minimizes shear and eliminates cavitation, both of which damage biological entities.

In the present implementation, biomimetic peristalsis is effected by the geometry and composition of the nanoantenna-shape memory gel composite and its surrounding architecture as well as the energy dynamics of electromagnetic induction.

Preferential retention of the microbe analyte(s) in the disclosed smart material system results from engineered transport of analyte to solid-fluid interfaces at which a sorptive interaction may occur. Examples of transport include bulk convection, diffusion, eddy flow, and dispersion. Examples of sorptive interactions include electrostatic, ionic, biospecific, hydrophilic, hydrophobic, and mixed mode. Effectiveness of transport and sorptive modes is highly dependent on the characteristics of the analyte (e.g., geometry, physicochemistry, composition) and the carrier fluid and matrix (e.g., physicochemical properties and composition of fluid, solid, and fluid-solid interfaces.) Novel transport and sorptive interaction chemistries and modes are described that facilitate preferential retention of targeted microbe analyte(s). Such transport and sorptive interaction chemistries and modes, such as those described in D. K Roper, S. Nakra, Adenovirus type 5 intrinsic adsorption rates measured by surface plasmon resonance, *Analytical Biochemistry* (2006), 348, 75-83, can be used in devices and methods described herein.

FIG. 1 illustrates an electromagnetically nanotunable shape memory gel system to collect microbes. As illustrated in FIG. 1(*a*), microbes (dark dots) are dispersed in a fluid adjacent to an architecture or container (cylinder) with shape memory gel (illustrated with cross-hatch) and uninduced nanoantenna (dark dots). In FIG. 1(*b*), an electromagnetic trigger induces (e.g., heats) nanoantenna which are concentrated at the gel periphery. In FIG. 1(*c*), nanoantenna induction densifies the shape memory gel in the peripheral region (darker cross-hatch), preventing backflow. In FIGS. 1(*d*) and 1(*d*), continued induction synergistically densifies the gel body, outputting microbe-free fluid above (at the output side of the gel) and inputting microbe-containing fluid below (at the intake side of the gel). In FIG. 1(*f*), the trigger is halted to relax the gel, retaining microbe at fluid-gel interface via inputting fluid. Then the cycle repeats to enrich microbe content. Enriched microbe is detected in situ or subsequent to discharge of retained microbes in carrier fluid.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A device for collecting and/or enriching one or more microbes, the device comprising:
- a shape memory gel; and
- a plurality of nanoantennas non-uniformly dispersed in the gel, wherein the nanoantennas are operable to receive an external signal and thereby induce a local change in state of the gel for retaining the one or more microbes in the gel.

2. The device of claim 1, wherein the local change in state is a local change in thermodynamic state of the gel.

3. The device of claim 1, wherein the gel is a crosslinked hydrogel.

4. The device of claim 1, wherein the gel comprises poly (N-isopropylacrylamide).

5. The device of claim 1, wherein the gel is a pH-responsive shape memory gel, a temperature-responsive shape memory gel, a pressure-responsive shape memory gel, a light-responsive shape memory gel, or an electrochemical-responsive shape memory gel.

6. The device of claim 1, wherein the local change in state induced by the nanoantennas is a local change in the internal energy, entropy, mass, chemical composition, fugacity, temperature, pH, pressure, and/or specific volume of the gel.

7. The device of claim 1, wherein the nanoantennas are formed from metal nanoparticles.

8. The device of claim 1, wherein the nanoantennas are present in the gel in a higher density in a peripheral region of the gel and in a lower density in an interior region of the gel.

9. The device of claim 8, wherein the peripheral region of the gel is adjacent one or more an intake side of the gel in fluid communication with a liquid analyte.

10. The device of claim 9, wherein the one or more microbes are dispersed in the liquid analyte.

11. The device of claim 1, wherein the gel is disposed in a container.

12. The device of claim 11, wherein the container is operable to place an intake side of the gel in fluid communication with a liquid analyte.

13. The device of claim 12, wherein the one or more microbes are dispersed in the liquid analyte.

14. The device of claim 1, wherein the local change comprises an increase in the density of the shape memory gel.

\* \* \* \* \*